United States Patent
Bazarov et al.

(10) Patent No.: US 6,651,503 B2
(45) Date of Patent: Nov. 25, 2003

(54) METHOD OF IN-TUBE ULTRASONIC FLAW DETECTION

(75) Inventors: Alexandr Jurievich Bazarov, Kolomna (RU); Alexandr Petrovich Desyatchikov, Kolomna (RU); Nikolai Alekseevich Karasev, Kolomna (RU); Sergei Pavlovich Kirichenko, Kolomna (RU); Andrei Mikhailovich Slepov, Kolomna (DE); Anatoly Valentinovich Smirnov, Kolomna (RU)

(73) Assignee: NGKS International Corp., Richmond Hill (CA)

( * ) Notice: Subject to any disclaimer, the term of this patent is extended or adjusted under 35 U.S.C. 154(b) by 0 days.

(21) Appl. No.: 10/144,622

(22) Filed: May 13, 2002

(65) Prior Publication Data

US 2002/0174722 A1 Nov. 28, 2002

(30) Foreign Application Priority Data

May 25, 2001 (RU) ........................ 2001114064

(51) Int. Cl.⁷ .............................................. G01N 29/04
(52) U.S. Cl. ........................................... 73/623; 73/602
(58) Field of Search ................... 73/623, 620, 622, 73/592, 598, 602, 628, 865.8; 702/35, 39

(56) References Cited

U.S. PATENT DOCUMENTS

| | | | | |
|---|---|---|---|---|
| 4,162,635 A | * | 7/1979 | Triplett et al. ........... | 73/623 |
| 4,559,610 A | * | 12/1985 | Sparks et al. ........... | 703/9 |
| 4,713,968 A | * | 12/1987 | Yale ...................... | 73/594 |
| 4,909,091 A | * | 3/1990 | Ellmann et al. ........... | 73/866.5 |
| 4,953,405 A | * | 9/1990 | Hara et al. ............... | 73/602 |
| 4,964,059 A | * | 10/1990 | Sugaya et al. ........... | 702/38 |
| 5,062,300 A | * | 11/1991 | Vallee .................... | 73/623 |
| 5,460,046 A | * | 10/1995 | Maltby et al. ............ | 73/623 |
| 5,497,661 A | * | 3/1996 | Stripf et al. ............. | 73/611 |
| 5,587,534 A | * | 12/1996 | McColskey et al. ....... | 73/623 |
| 5,635,645 A | * | 6/1997 | Ottes et al. ............. | 73/623 |
| 5,648,613 A | * | 7/1997 | Kiefer .................... | 73/611 |
| 6,253,615 B1 | * | 7/2001 | Simmonds et al. ........ | 73/579 |
| 6,339,993 B1 | * | 1/2002 | Comello et al. .......... | 104/138.2 |
| 6,472,883 B1 | * | 10/2002 | Burnett .................. | 324/534 |
| 6,571,634 B1 | * | 6/2003 | Bazarov et al. .......... | 73/623 |

* cited by examiner

*Primary Examiner*—Hezron Williams
*Assistant Examiner*—Jacques Saint-Surin
(74) *Attorney, Agent, or Firm*—Welsh & Katz, Ltd.

(57) ABSTRACT

The claimed method of in-tube ultrasonic flaw detection of pipelines is effected, in accordance with one embodiment, by placing inside a pipeline an inspection pig or flaw detector having ultrasonic transducers, devices for measurements, processing and storage of the measured data. During the pig travel, the transducers emit probing ultrasonic pulses and receive the reflected pulses corresponding to said probing pulse thus deriving data on the time intervals corresponding to the transit time of said pulses, the measured data being converted and stored. In the process of the data conversion a sequence of values of the transit time of the ultrasonic pulses is formed, an area of values of a certain width is derived, in which the maximum number of the obtained values of said sequence is located, the range of values uniquely corresponding to the found area of values, in which at least one value relates to the derived area of values, the number of obtained values of the sequence laying in said range of values is recorded in said storage device together with a code uniquely corresponding to said area of values and/or said range of values. The obtained values beyond the limits of said range of values are directly recorded in the digital data storage device. The implementation of the claimed method allows one to, for example, increase the efficiency of compression of the ultrasonic data, especially when detecting the flaws in the linear part of trunk pipelines including pipe with different nominal thickness of the walls, and in the presence of flaws such as <<lamination>> and similar flaws in the pipeline.

13 Claims, 4 Drawing Sheets

METHOD OF IN-TUBE ULTRASONIC FLAW DETECTION

BACKGROUND OF THE INVENTION

The present invention generally relates to a method of ultrasonic flaw detection of long-distance pipelines such as, for example, trunk oil pipelines, oil-products pipelines, and gas pipelines. More specifically, acoustic communication between one or more ultrasonic transducers and the pipe walls (for example, by means of a fluid plug) is provided by passing inside the pipeline a so-called "pig," or an inspection probe, which is put into the pipeline and is conveyed by the fluid flow in the pipeline. Typical inspection pigs have built-in transducers, measuring instruments, devices for conversion and recording of the measured data, and a device that acquires digital data during the pig travel and processes the obtained data to detect flaws in the pipe walls and to determine the parameters of the detected flaws, as well as their position in the pipeline.

Known in the art is a method of in-tube ultrasonic flaw detection (U.S. Pat. No. 4,162,635) carried into effect by passing inside a pipeline a inspection pig having ultrasonic transducers, means for measurement, processing and storage of the measurement data. The traveling pig emits ultrasonic probing pulses towards the walls and receives the respective reflected ultrasonic pulses.

Also known in the art is a method of in-tube ultrasonic flaw detection (U.S. Pat. Nos. 5,587,534, 4,964,059, 5,497,661, 5,062,300) using a thickness metering technique. In accordance with this technique, an inspection pig that accommodates ultrasonic transducers and means for measurement, processing and storage of the measured data is passed inside the pipeline. During the pig travel the pulse transit time is measured by emitting ultrasonic probing pulses and by receiving the ultrasonic pulses reflected from the internal and external walls of the pipeline.

In accordance with these known techniques, making measurements with accuracy sufficient for inspection, identification of flaws, and determination of their parameters requires use of high-capacity memory devices. However, the pig traveling inside a pipeline has a limited volume for arrangement of data storage devices.

Several data transfers accompany the use of standard devices for compressing the data stored in files, irrespective of the physical nature of these data. At a low amount of transfers the compression is ineffective. The use of archiving algorithms such as Zip, Arj, Rar, and other efficient compression routines is accompanied by plenty of transfers of the compressed data. In so doing the amount of transfers and, respectively, the archiving time depends on the type and character of the data and is not restricted from above. For this reason, the time of data processing can exceed the reserved time and lead to errors in subsequent processing of the data and, respectively, to loss of some data.

Also known in the art is a method of in-tube ultrasonic flaw detection (U.S. Pat. No. 5,460,046 using the thickness metering method. In accordance with this technique, a pig (flaw detector) is passed inside the pipeline, said pig carrying ultrasonic transducers and devices for measuring, processing and storing the measured data. The measured data are generated by emitting ultrasonic probing pulses during the pig travel, receiving the respective ultrasonic pulses reflected from the internal and external walls of the pipeline, and by measuring the pulse transit time.

This method is characterized in that the values corresponding to the pipeline wall thickness within permissible limits are neglected, and what are recorded are only the values corresponding to the wall thickness below a permissible value.

During the in-tube ultrasonic flaw detection of pipelines, which have pipes whose thickness is beyond the permissible limits for the pipeline being tested, the measured data of the part of the pipeline corresponding to such pipes are recorded in a full scope even if they have no flaws.

Known in the art is another method of in-tube ultrasonic flaw detection (U.S. Pat. No. 4,909,091) by passing an inspection pig inside a pipeline, said pig carrying ultrasonic transducers, devices for measuring, processing and storing the measured data by emitting ultrasonic probing pulses during the pig travel and receiving the respective ultrasonic pulses reflected from the internal and external walls of the pipeline, and measuring the pulse transit time.

This method is characterized in that the measured successive values, which are rejected within a predetermined range of values, are recorded as a function of a number of successive values.

When testing the pipelines having pipes of different types and with a different thickness of the wall (with a difference in the wall thickness exceeding the error of thickness measurement and, respectively, the preset range width) the data measured in the part of the pipeline corresponding to the rated wall thickness for the pipes of a given section are not within the predetermined range and are not compressed.

The most similar with claimed method is a known in the art (U.S. Pat. No. 5,635,645) method of in-tube ultrasonic flaw detection of pipelines by passing inside the pipeline an inspection pig (flaw detector) carrying ultrasonic transducers, means for measurements, processing and storing the measured data, by emitting ultrasonic probing pulses and receiving the reflected pulses corresponding to said probing pulses, by obtaining data on the time intervals corresponding to the transit time of said pulses, and by conversion and storage of the measured data in the process of passing inside the pipeline.

During the data conversion in this method a sequence of the obtained values of the pulse transit time is formed, the number of obtained values of said sequence within a certain range being calculated and recorded in a storage device.

This method is characterized in that the range of values is set by a nominal value and a window symmetric relative to the nominal value. The nominal value is determined for each sequence of the obtained values by averaging the sequence values.

The main disadvantage of the known method is that in the presence of elongated lamination of metal in the wall of the pipe being tested or other flaws, the average value, as a rule, is beyond the range corresponding to rated pipeline wall thickness and beyond the range corresponding to the metal lamination. As a result, neither the values corresponding to the rated wall thickness nor the values corresponding to the laminations are in the range near the average value and, therefore, are not compressed.

The claimed invention is a method of in-tube ultrasonic flaw detection of pipelines is effected by passing inside a pipeline an inspection pig carrying ultrasonic transducers, devices of measuring, processing and recording the measured data (devices for measurements, processing and measured data storage), by emitting ultrasonic probing pulses during the pig travel and receiving the reflected pulses corresponding to said probing pulses, by obtaining data on the time intervals corresponding to the transit time of said pulses, by converting and recording (conversion and storage of) the measured data; during said data conversion a sequence of the obtained values of the transit time of the ultrasonic pulses is formed, the number of obtained values of said sequence within a certain (definite) range being calculated and recorded in a storage device.

The present invention differs from the prior art in a number of material respects. For example, in the process of data conversion, an area of values of a certain width is found, which has the maximum number of obtained values of said sequence, said range of values is found, in which at least one value relates to the found area of values. The number of obtained values of said sequence within said range is recorded in the storage device together with a code uniquely corresponding to said area of values and/or said range of values.

One of advantages that is obtained as a result of effecting the claimed invention is, for example, a decrease of size of the storage devices used when scanning the pipeline of a given length or an increase of the pipeline distance inspected for one pig travel at a given amount of the stored data.

The mechanism for attaining said technical result is that, for example, when processing the measured data corresponding to the laminations in the wall of the pipe with extended corrosion damage, the data sequences corresponding to the joint of pipes with different wall thickness, according to an exemplary embodiment of the claimed method, a range is found corresponding to the most probable value in the sequence of values.

This range corresponds either to the nominal thickness of the pipe wall (of whatever thickness it might be) or to the wall lamination, or to nominal thickness of the wall of one of the pipes in the joint of pipes of different thickness, or to the most frequently repeating value of depth of corrosion of a large extent. In all said and similar cases, the most frequently repeating values (within the range) in the sequence are compressed.

The obtained values that do not fall in said range of values are recorded directly in the digital data storage device.

As a still further exemplary development of the claimed invention, an average value of the range of values is determined, the digital data storage device is used for recording the retrieved average value of the range of values and the number of obtained values following in succession in a sequence laying in said range of values.

In a general case, the required area of values and the range of values may not coincide. Thus, the range width defines the inspection pig resolution and the amount of compressed data. The width of the required area of values determines the time of execution of the area search algorithm.

Said range of values uniquely corresponds to said area of values according to a predetermined (preset) rule.

In one exemplary embodiment of the claimed method, said range of values coincides with the found area of values. Such an embodiment allows, for example, one to achieve the highest degree of compression with no restriction on the time of execution of the algorithm.

In still another embodiment of the method the width of said range of values is directly proportional to the width of the found area of values. Such an embodiment allows one to optimize the width of a required area of values to match inspection pig hardware capability on the data processing without changing the width of said range of values and, respectively, the inspection pig resolution.

In order to find the above-mentioned range of values, some part of the obtained values from said sequence is taken into account. It is preferable to retrieve said range of values from a certain interval of the obtained values of said sequence corresponding to the ultrasonic pulses reflected from the area of pipeline wall.

Such a restriction allows one to exclude from the analysis on determining the most probable obtained values the data carrying no physical information on the wall thickness, for example, data corresponding to the ultrasonic pulses, reflected from the internal wall of the pipeline and not reflected from the external wall, as well as the ultrasonic pulses reflected from the media interface beyond the pipeline external wall.

In one exemplary application, the width of above range of values makes 0.3–10% of the maximum permissible obtained value in said sequence. The execution of the method at a smaller width of the range results in an unjustified decrease of the resolution (below the sufficient resolution for flaw detection) and, therefore, an increase of the amount of compressed data. At a greater width of the range the resolution is increased respectively, especially when inspecting the trunk gas pipelines, and the detection of flaws in the wall is complicated.

The amount (quantity) of the obtained values in said sequence of values is within a range of 200–5000. A sequence of digital values of the transit time of said ultrasonic pulses is formed in the process of measurements, the digit capacity of said digital values being not less than 5. In the preferable embodiment, the digit capacity of said digital values is not less than 7. This allows one to obtain resolution of 0.2 mm at a wall thickness of up to 25 mm.

At a certain low number of the obtained values in a sequence, the efficiency of the method at the faultless sections of the pipeline with a constant wall thickness is reduced because the number of formed sequences and, respectively, the number of recordings in a storage device per pipeline unit length of the grows up.

At a higher number of the obtained values in a sequence corresponding to about 16 m along the pipeline length, the efficiency of the method on the pipeline sections with multiple flaws such as "lamination" or the like, drops down because in the presence of several flaws of the "lamination" type per one sequence at the lamination extent greater than the extent of the faultless section of the pipeline, those values are compressed that correspond only to one most extended lamination.

During the measurements the ultrasonic pulses are received that are reflected from the internal and external walls of the pipeline, and the pulse reflected from the pipeline internal wall triggers the counter to count the time interval between the moment of arrival of the pulse reflected from the internal wall and the moment of arrival of the pulse reflected from the external wall of the pipeline. The above time intervals are measured by the moments of exceeding the predetermined threshold by an electric signal from the ultrasonic transducer corresponding to the received ultrasonic pulse.

BRIEF DESCRIPTION OF THE DRAWINGS

The benefits and advantages of the present invention will become more readily apparent to those of ordinary skill in the relevant art after reviewing the following detailed description and accompanying drawings, wherein.

During the research aimed at solutions of the problem of increase the degree of data compression we used the equipment developed by the <<Neftegazkomplektservis>> Private Stock Company. This equipment includes in-tube ultrasonic pigs (flaw detectors) for inspection of pipelines with a nominal diameter of 10" to 56" and with a variable wall thickness allowed us to develop the claimed method of flaw detection.

The pigs or flaw detectors in a preferable embodiment occupy of about 85% of the nominal diameter of the pipeline and a minimum passable radius of turn of about 1.5 pipeline diameter. The inspection pigs operate at a temperature of 0° C. to +50° C. and withstand the pumped medium pressure of up to 80 atmospheres. The pigs are provided with explosion protection such as <<Explosion-proof shell>> and <<Special explosion-proof arrangement>> at an input electric current of less than 9 A.

Figure 1:
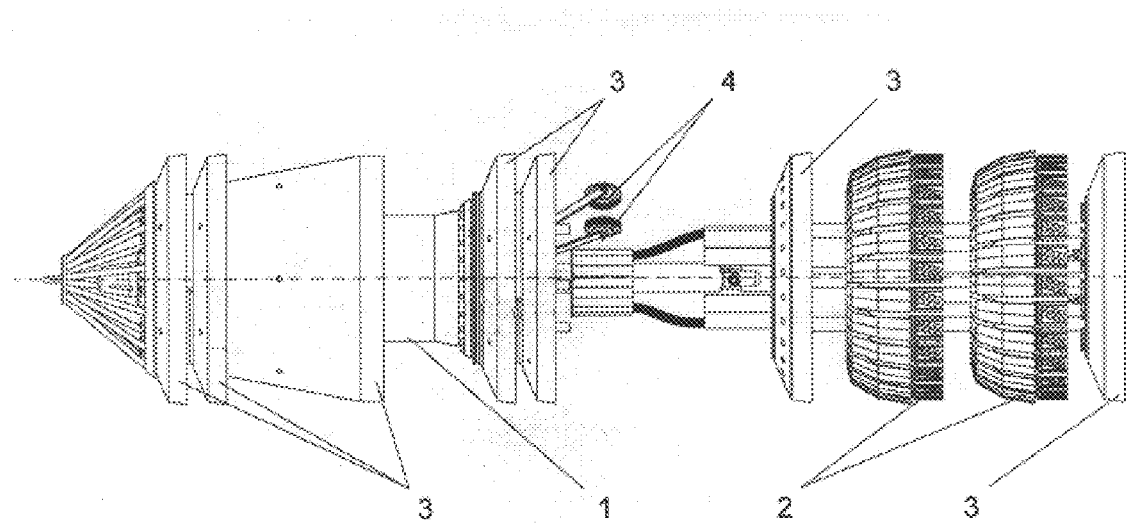
FIG. 1 illustrates an embodiment of the in-tube ultrasonic flaw detector that incorporates one example of the invention that is disclosed and claimed herein.

The in-tube ultrasonic flaw detector for inspection of pipelines with a diameter of 38" to 56" and with a wall thickness of 4 to 23.5 mm in one of the preferable embodiments is shown in FIG. 1. The device comprises a body 1, forming an explosion-proof shell accommodating a power supply and electronic equipment for measurements, processing and storage of the obtained measured data on the basis of an on-board computer controlling the operation of the inspection pig during its travel inside the pipeline. The power supply consists of storage batteries or galvanic cells having capacity of up to 1000 ampere-hours.

The tail part of the inspection pig accommodates ultrasonic transducers 2, alternately emitting and receiving ultrasonic pulses. The polyurethane sealing rings 3 mounted on the pig body provide centering of the pig inside the pipeline and its movement with the flow of the fluid medium pumped through this pipeline. The wheels of the odometers 4 installed on the pig body are pressed to the internal wall of the pipeline. During the pig travel the information on the passed distance measured by the odometers is recorded in the storage device of the on-board computer and after performing the diagnostic scanning and processing of the accumulated data allows one to determine the position of the flaws on the pipeline and, respectively, the place of subsequent excavation and repair of the pipeline.

The device operates as follows.

Figure 2:
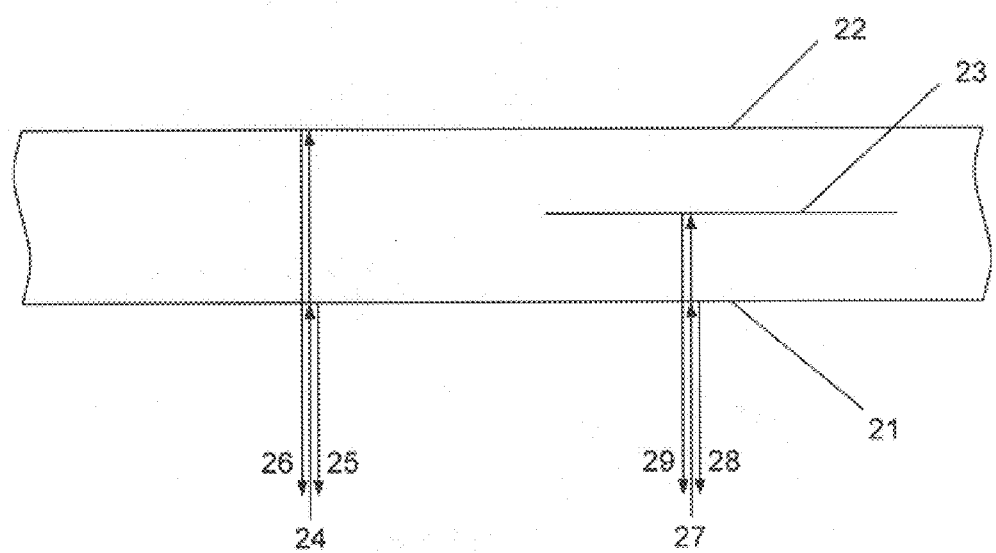
FIG. 2 is a diagram illustrating the transfer of the ultrasonic probing pulses on a faultless section of the pipe and on a faulty section with a flaw such as "lamination"

The inspection pig is placed into the pipeline and the pump for pumping the product (oil, oil product) through the pipeline is switched on. In the process of travel of the inspection pig inside the pipeline the ultrasonic transducers periodically emit ultrasonic pulses 24, 27 (FIG. 2) which are partially reflected from the pipeline internal wall 21, from the external wall 22 or from the flaw area 23, for example, metal lamination in the pipe wall. Having emitted the ultrasonic pulses, the ultrasonic transducers switch to the mode of reception of the reflected pulses and receive the pulses 25, 28 reflected from the internal wall, the pulses 26 reflected from the external wall or the pulses 29 reflected from said flaw area.

The electric pulse triggering the ultrasonic transducer for emitting ultrasonic pulses, simultaneously triggers the counter to count the time interval between the moment of emitting the ultrasonic pulse and moment of receiving the ultrasonic pulse reflected from the internal wall of the pipe. The electric pulse detected by the signal processing devices as an ultrasonic pulse, received by the ultrasonic transducer, stops the counter counting the time interval corresponding to the travel of the ultrasonic pulse to the internal wall and back and simultaneously triggers the counter to count the time interval between the moment of receiving the ultrasonic pulse reflected from the internal wall of a pipe and the moment of reception of the respective ultrasonic pulse reflected from the external wall of the pipe or from the flaw area.

The obtained digital data on the time intervals corresponding to the transit time of the ultrasonic pulses are converted and recorded in the digital data storage device of the on-board computer.

In the process of the data conversion there is formed a sequence of 512 seven-bit digital values of the ultrasonic pulse transit time. After that an area of values having a width of about 2% of the maximum allowable value in a sequence and the amount of sequence values are found. A range of values for compression is found, in which the preferable range coincides with the found area of values. Further operation consists in calculation and recording in the storage device of the number of sequence values laying in the range of the greatest number of values of said sequence (as well as about 2% of maximum value in the sequence).

Recorded in the digital data storage device is the average value of said range (in this case coinciding with the average value of the found area of values) and the quantity of the successive values within said range of values. The information on the average value of the range and on the preset numerical value of the range width allows the found range to be uniquely identified.

The measured data are processed and recorded in the storage device of the on-board computer based of solid-state memory elements.

Figure 3:
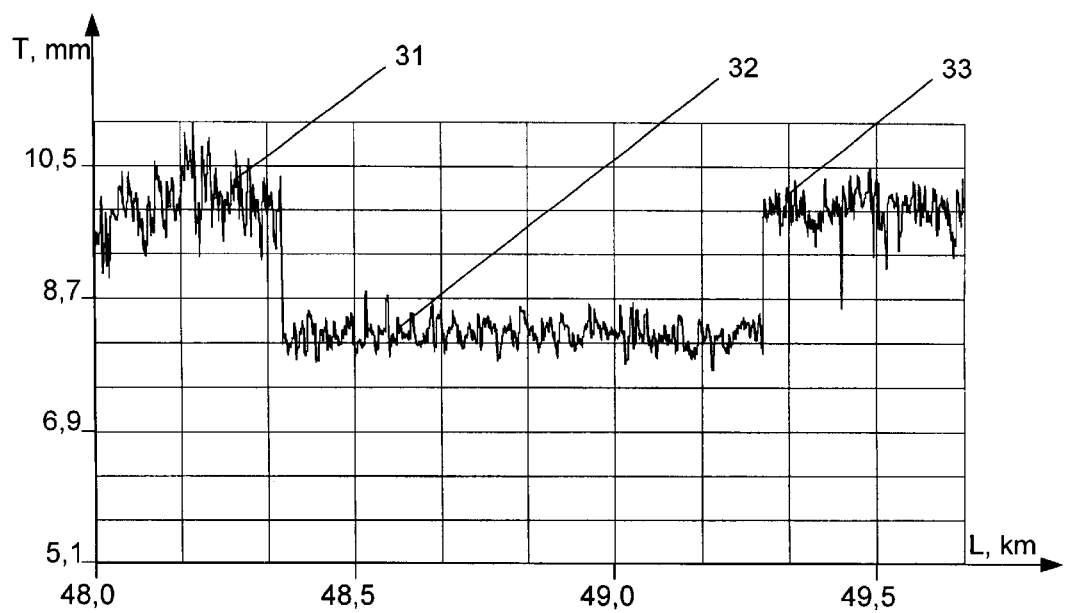
FIG. 3 is a graph that illustrates the dependence of the pipeline wall thickness on the distance passed inside the pipeline along a section of the inspected pipeline measured by the ultrasonic flaw detector.

FIG. 3 illustrates the dependence of the pipeline wall thickness on the pipeline length. The sections 31, 32 and 33 in FIG. 3 correspond to the sections of the pipeline, on which the pipes with different wall thickness are used: 10 mm for section 31; 8.2 mm for section 32 and 10 mm for section 33. The difference in the nominal thickness makes 1.8 mm, whereas the resolution achieved in the claimed invention by the wall thickness is 0.2 mm. It is obvious that the predetermined permissible range of the wall thickness values, in which the measured values are discarded, cannot be used for inspection of such pipelines. On the other hand, the implementation of the claimed method allows, for example, one to compress the data corresponding to the pipes of each of said types, including the sections at joints of pipes having different thickness of the walls.

Figure 4:
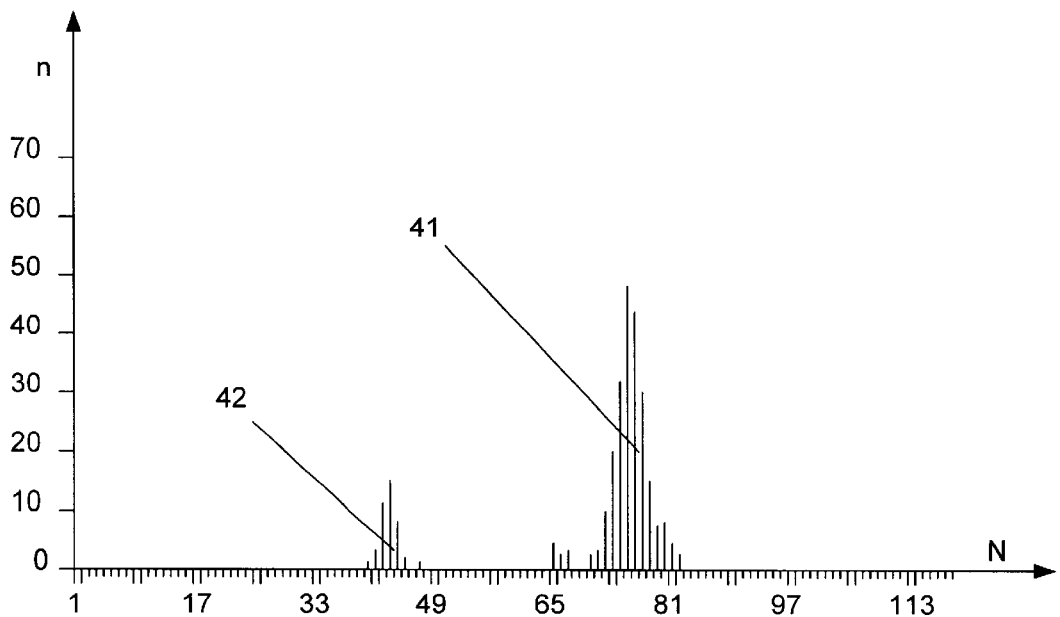
FIG. 4 is a histogram that illustrates allocation of the measured values of the pipeline wall thickness in a sequence of values corresponding to the inspected section of the pipeline having a fault such as "lamination"

FIG. 4 is a histogram illustrating the distribution of the measured values of the pipeline wall thickness in a sequence of 512 values measured by one of the ultrasonic transducers corresponding to the inspected section of the pipeline about 1.7 M with a flaw known as "lamination". The digital values of the transit time of the ultrasonic pulses in the pipeline wall are plotted on the axis N. The density of the transit time values (the quantity of every digital value-in the sequence) is plotted on the axis n. In this embodiment each digital value corresponds to the interval of real (physical) values of the width equal to unity. The greatest part of values in the sequence 41 (FIG. 4) corresponds to the nominal value of the pipeline wall thickness with an average value 75, in which case a part of the values (position 42) with an average value 43 correspond to the "lamination" flaw of the pipeline wall with a total length of about 25 cm. The determination of the range for compression (in accordance with the method of prior art U.S. Pat. No. 5,635,645) by the average value in the sequence gives an average value 67.

Having the width range of 3 values and using the found average value, about 1% data in the sequence will be compressed (in accordance with the method of prior art U.S. Pat. No. 5,635,645).

In accordance with one aspect of the claimed method, a range is determined (in one of preferable embodiments with a width of 3 values), in which the maximum amount of values in said sequence is located, and the found range for the represented sequence of values is within 74 to 76. In so doing about 25% data in the sequence are compressed.

In another embodiment, at a width of the range of 9 values and using the found average value (in accordance with the method of prior art U.S. Pat. No. 5,635,645), about 6% data in the sequence will be compressed.

In the claimed method a range of thickness of 9 values is determined, which includes the maximum quantity of values of said sequence and the found range for the presented sequence of values lays within the limits from 72 to 80. In so doing about 78% data in the sequence are compressed.

After the inspection of a given section of the pipeline has been completed, the pig (flaw detector) is extracted from the pipeline and the data accumulated during the diagnostic pig travel are transferred to a separate computer.

The subsequent analysis of the recorded data allows one to identify flaws of the pipeline wall and to determine their position on the pipeline for the purpose of subsequent repair of the faulty sections of the pipeline.

Figure 5:
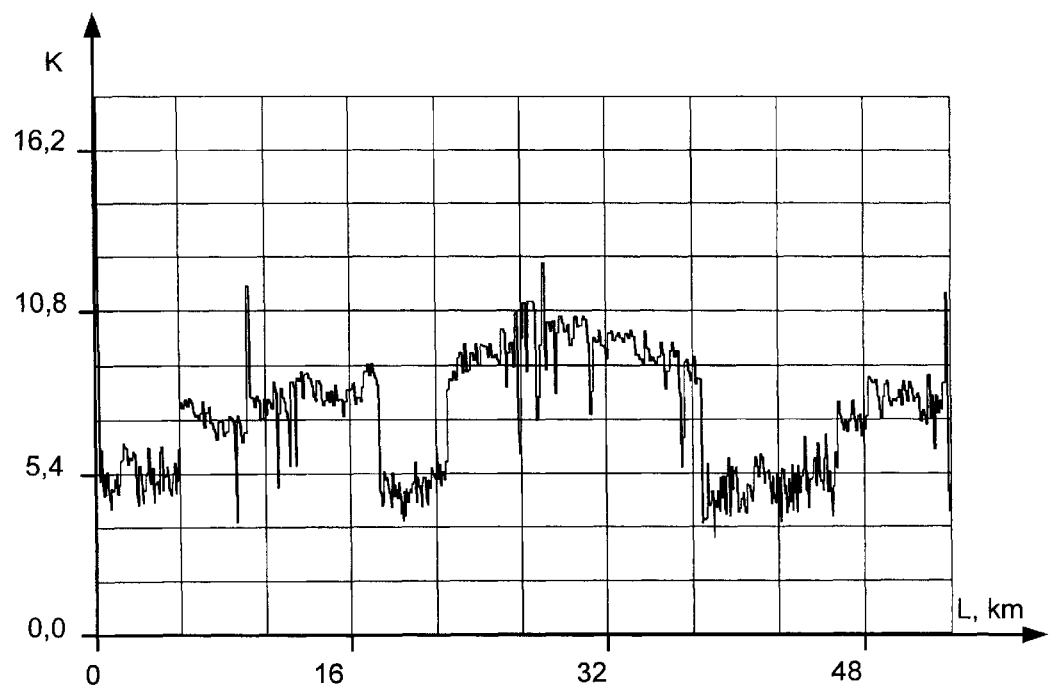
FIG. 5 is a graph that illustrates the dependence of the compression ratio on the distance passed inside the pipeline for some section of the inspected pipeline.

FIG. 5 illustrates the dependence of the compression ratio K on the distance L passed inside the pipeline for some section of the inspected pipeline. The compression ratio K is determined as a ratio of the volume occupied by the obtained ultrasonic data directly recorded in the storage device to the volume occupied by the obtained ultrasonic data recorded in the storage device after compression.

Figure 6:
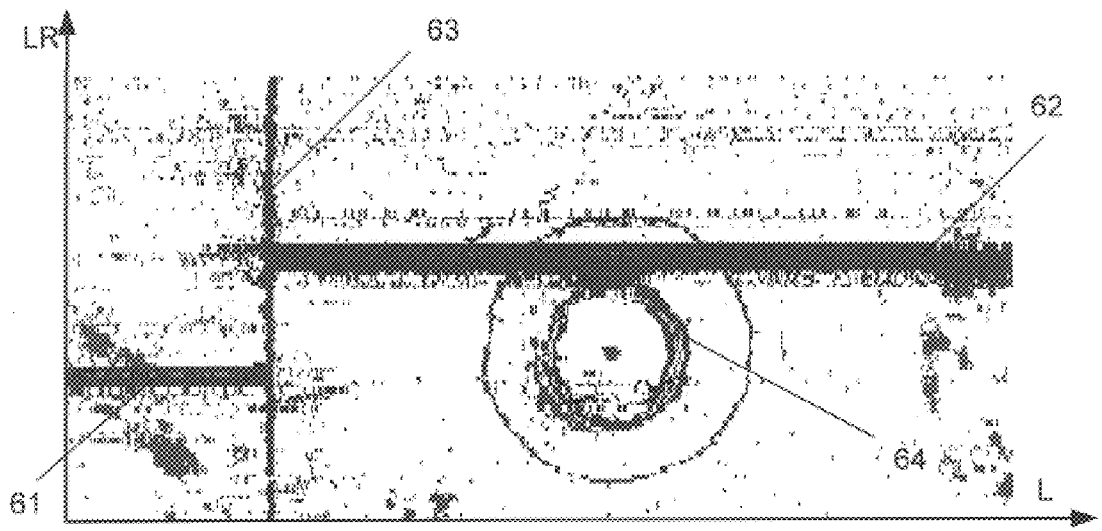
FIG. 6 is a graphic representation of the measured data on the pipeline wall thickness for some section of the inspected pipeline allowing the weld joints to be identified.
Figure 7:
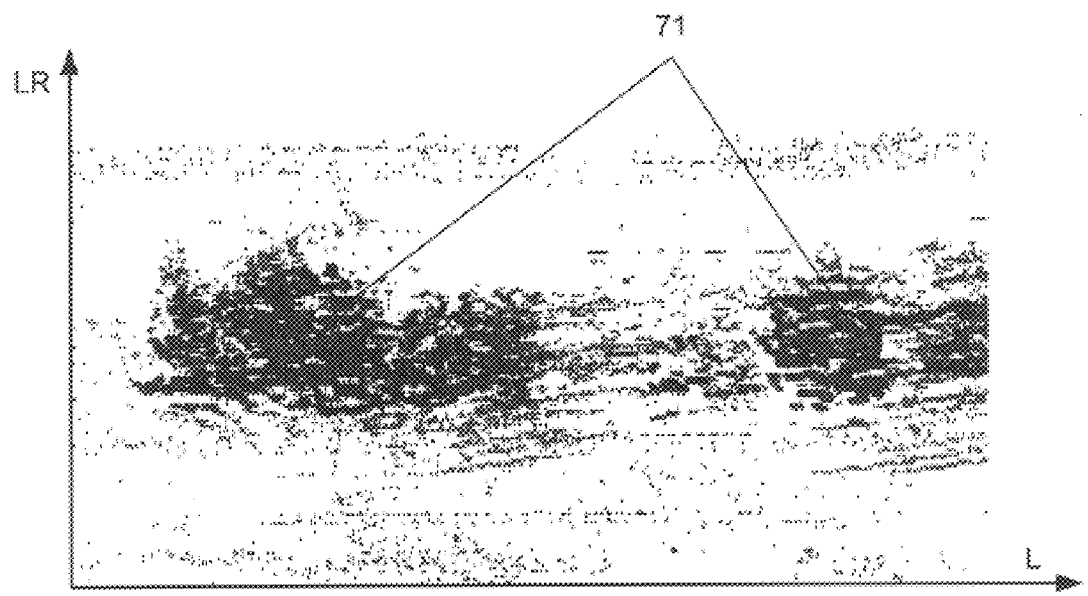
FIG. 7 is a graphic representation of the measured data on the pipeline wall thickness for some section of the inspected pipeline allowing the corrosion loss of metal to be identified.

FIGS. 6 and 7 illustrate the fragments of the graphic representation of the data obtained as a result of the diagnostic travel of the pig allowing the specific features of the pipeline and the wall flaws to be identified. The pipeline length along its axis is plotted on the axis L of FIG. 7 and the length along its perimeter is plotted on the axis LR. The black dots on the image show that at these spots on the pipe the difference between the measured value of the wall thickness and the nominal value for the given section of the pipeline exceeds the preset threshold value. FIG. 6 illustrates the characteristic features of the pipelines: longitudinal welded joints 61 and 62 of the pipes, a welded joint between the pipes 63, and a plunger 64. Shown in FIG. 7 are typical corrosive flaws 71 on the pipe detected as a result of performing the in-tube ultrasonic flaw detection by the claimed method.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A method of in-tube ultrasonic flaw detection of pipelines by passing inside the pipeline an inspection pig carrying ultrasonic transducers, devices for measurements, processing and measured data storage, by emitting probing ultrasonic pulses during the pig travel and receiving the reflected pulses corresponding to said probing pulses, by obtaining data on the time intervals corresponding to the transit time of said pulses, by conversion and storage of the measured data; during said data conversion a sequence of the obtained values of the transit time of the ultrasonic pulses is formed, the number of obtained values of said sequence within a certain range is calculated and recorded in a storage device, wherein in the process of data conversion an area of values of a certain width is found, which has the maximum number of obtained values of said sequence, said range of values is found, in which at least one value relates to the found area of values, said number of obtained values of said sequence within said range is recorded in said storage device together with a code uniquely corresponding to said area of values and/or said range of values.

2. A method according to claim 1, wherein the obtained values beyond the range specified in claim 1 are recorded directly in the digital data storage device.

3. A method according to claim 1, wherein an average value of the range of values specified in claim 1 is determined, the digital data storage device is used for recording the retrieved average value of the range of values specified in claim 1 and the number of obtained values following in succession in a sequence laying in said range of values.

4. A method according to claim 1, wherein the range of values specified in claim 1 uniquely corresponds to the area of values specified in claim 1 by a preset rule.

5. A method according to claim 1, wherein the width of the range of values specified in claim 1 is directly proportional to the width of the area of values specified in claim 1.

6. A method according to claim 1, wherein the range of values specified in claim 1 coincides with the area of values specified in claim 1.

7. A method according to claim 1, in which, in order to find the range of values specified in claim 1, a part of the obtained values from the sequence specified in claim 1 is taken into account.

8. A method according to claim 1, wherein the range of values specified in claim 1 is retrieved from a certain interval of the obtained values of the sequence specified in claim 1 corresponding to the ultrasonic pulses reflected from the area of the pipeline wall.

9. A method according to claim 1, wherein the width of the range of values specified in claim 1 makes 0.3–10% of the maximum permissible obtained value in the sequence specified in claim 1.

10. A method according to claim 1, wherein the quantity of the obtained values in the sequence of values specified in claim 1 makes 200–5000.

11. A method according to claim 1, wherein during the measurements there is formed a sequence of digital values of the transit time of the ultrasonic pulses specified in claim 1, the digit capacity of said digital values being equal to at least 7.

12. A method according to claim 1, wherein during the measurements the ultrasonic pulses reflected from the internal and external walls of the pipeline are received, the pulse reflected from the internal wall of the pipeline triggers the counter to count the time interval between the moment of arrival of the pulse reflected from the internal wall of the pipeline and the moment of arrival of the pulse reflected from the external wall of the pipeline.

13. A method according to claim 1, wherein the time intervals specified in claim 1 are measured by the moments of exceeding the predetermined threshold by the electric signal from the ultrasonic transducer corresponding to received ultrasonic pulse.

* * * * *